(12) United States Patent
Spenser et al.

(10) Patent No.: US 10,342,928 B2
(45) Date of Patent: Jul. 9, 2019

(54) SYRINGE CRADLE

(71) Applicant: INJECTEC LTD, Herzeliya (IL)

(72) Inventors: Benjamin Spenser, Bat Shlomo (IL);
Gonen Somekh, Kerem Maharal (IL);
Gershon Goldenberg, Pardes Chana (IL); Tsahi Vider, Herzelia (IL)

( * ) Notice: Subject to any disclaimer, the term of this patent is extended or adjusted under 35 U.S.C. 154(b) by 715 days.

(21) Appl. No.: 14/376,546

(22) PCT Filed: Jan. 24, 2013

(86) PCT No.: PCT/IL2013/050063
§ 371 (c)(1),
(2) Date: Aug. 4, 2014

(87) PCT Pub. No.: WO2013/114357
PCT Pub. Date: Aug. 8, 2013

(65) Prior Publication Data
US 2015/0025502 A1  Jan. 22, 2015

Related U.S. Application Data

(60) Provisional application No. 61/633,004, filed on Feb. 3, 2012.

(51) Int. Cl.
*A61M 5/315* (2006.01)
*A61M 5/24* (2006.01)

(52) U.S. Cl.
CPC ...... *A61M 5/3158* (2013.01); *A61M 5/31501* (2013.01); *A61M 5/31511* (2013.01); *A61M 5/31593* (2013.01); *A61M 5/31595* (2013.01); *A61M 5/24* (2013.01)

(58) Field of Classification Search
CPC ............ A61M 5/31593; A61M 5/3158; A61M 5/31501; A61M 5/31511; A61M 5/24; A61M 5/31595; A61M 5/315
USPC ...................................................... 604/197
See application file for complete search history.

(56) References Cited

U.S. PATENT DOCUMENTS

| | | | |
|---|---|---|---|
| 4,936,833 A * | 6/1990 | Sams | A61M 5/31553 222/391 |
| 6,276,568 B1 * | 8/2001 | Brotspies | B65D 83/75 222/321.6 |
| 7,641,637 B2 | 1/2010 | Gerondale et al. | |
| 2007/0191784 A1 * | 8/2007 | Jacobs | A61M 5/31555 604/224 |

(Continued)

FOREIGN PATENT DOCUMENTS

| EP | 0295075 | 12/1988 |
|---|---|---|
| WO | WO 20055097240 | 10/2005 |
| WO | WO 2006020756 | 2/2006 |

*Primary Examiner* — Imani N Hayman
*Assistant Examiner* — Tiffany Legette
(74) *Attorney, Agent, or Firm* — Browdy and Neimark, P.L.L.C.

(57) ABSTRACT

A syringe cradle for holding a syringe, the syringe cradle comprising a syringe holder at a proximal end for engaging a barrel of a syringe and a rider for pressing on a plunger of the syringe, a cylindrical body for surrounding the syringe, a distal cap for closing a distal end of the cylindrical body, a stepwise advancing mechanism for advancing the rider along the cylindrical body towards the proximal end, and a stopping mechanism to prevent the rider from moving backwards towards the distal end of the cylindrical body.

14 Claims, 7 Drawing Sheets

(56) References Cited

U.S. PATENT DOCUMENTS

2008/0287873 A1* 11/2008 Liberatore .......... A61M 5/1456
604/131

* cited by examiner

SYRINGE CRADLE

PRIORITY INFORMATION

This National Stage Application claims priority to U.S. Provisional Application No. 61/633,004 filed on Feb. 3, 2012.

BACKGROUND

Syringes are widely used for injecting fluids into a patient's body. Syringes may be used for injecting into a blood vessel, into the skin tissue or into a muscle. Syringes may also be used to withdraw a sample of body fluid, such as amniotic fluid or blood, for example.

Essentially, a syringe consists of a cylindrical barrel with a narrow opening at one end, and a cylindrical plunger that tightly fits inside the barrel. A hollow needle may be fitted to the narrow opening. Raising the plunger in the barrel causes a suction pressure, and if the narrow opening or a hollow needle attached thereto is submerged in a fluid, the fluid is sucked into the barrel. Depressing the plunger causes fluid to be ejected from the syringe. Syringes are often marked with a graduated scale, so that exact quantities of fluid may be sucked in or ejected.

Syringes are available in different sizes. One common size is a 1 ml syringe that is typically marked with a scale into 0.1 ml sections. Each of these is divided into 0.02 ml subsections and such a syringe may be used to inject small doses such as 0.02 ml or 0.1 ml doses.

One application for micro syringes is to inject botulinium toxin or "botox". Botulinium toxin was first used in medical applications for treating strabismus ("crossed eyes"), a condition in which the eyes are not properly aligned with each other, and blepharospasm, which is an uncontrollable blinking disorder.

Dr. Richard Clark and the husband and wife team of J D and J A Carruthers pioneered use of botulinium toxin for treating wrinkles and frown lines.

In April 2002, the FDA announced regulatory approval of botulinum toxin type A (Botox Cosmetic) to temporarily improve the appearance of glabellar lines, which are the moderate-to-severe frown lines that may appear between the eyebrows. Subsequently, cosmetic use of botulinum toxin type A has become widespread. The results of cosmetic procedures vary, but can last up to eight months.

BTX-A is now a common treatment for muscles affected by the upper motor neuron syndrome (UMNS), such as cerebral palsy, for muscles with an impaired ability to effectively lengthen. Muscles affected by UMNS frequently are limited by weakness, loss of reciprocal inhibition, decreased movement control and hypertonicity (including spasticity). Joint motion may be restricted by severe muscle imbalance related to the syndrome, when some muscles are markedly hypertonic, and lack effective active lengthening. Injecting an overactive muscle to decrease its level of contraction can allow improved reciprocal motion, so improved ability to move and exercise.

BTX-A has also been approved for the treatment of severe primary axillary hyperhidrosis which is an excessive underarm sweating disorder.

Botulinum toxin type B (BTX-B) received FDA approval for treatment of cervical dystonia on Dec. 21, 2000. Trade names for BTX-B are Myobloc in the United States, and Neurobloc in the European Union.

Onabotulinumtoxin A (trade name Botox) received FDA approval for treatment of chronic migraines in 2010. The toxin is injected into the head and neck to treat these chronic headaches. Since then, several randomized control trials have shown botulinum toxin type A to improve headache symptoms and quality of life when used prophylactically Where the Botulinum toxin is injected into specific muscle tissue, a multiple number of small doses are injected in independent needle insertions into same area of the patient's muscle. The scale of each independent injection can vary from 0.1 ml. to 0.02 ml. the commonly used syringe is a 1 ml. syringe, meaning in some cases up to 50 small injections are drawn from one syringe. The technique that is currently used depends on the operator's skills and expertise. The operator needs to inject the portions by looking at the indication lines on the syringe body, but even so it is difficult to inject precise portions into the muscle. A disadvantage of the technique is that the operator is obliged to keep eye contact with the syringe rather than looking at the patient's skin or muscle while injecting. Furthermore, because of the difficulty to inject accurate doses of such a small size, operators often dilute the concentrated drug with saline and inject larger portions of the diluted drug. This technique improves the ability to inject accurate dosages of the drug but requires the operator to inject a larger quantity of fluid which is fairly quickly dispersed. The amounts injected and the ensuing results may be less than optimal.

SUMMARY OF INVENTION

A first aspect of the invention is directed to a syringe cradle for holding a syringe, the syringe cradle comprising a syringe holder at a proximal end for engaging a barrel of a syringe and a rider for pressing on a plunger of the syringe, a cylindrical body for surrounding the syringe, a distal cap for closing a distal end of the cylindrical body, a stepwise advancing mechanism for advancing the rider along the cylindrical body towards the proximal end, and a stopping mechanism to prevent the rider from moving backwards towards the distal end of the cylindrical body.

In one embodiment, the stepwise advancing mechanism comprises a push button coupled to a first ratchet rack by a neck passing through an aperture in the distal cap and a spring configured to urge the push button away from the distal cap, and a first toothed prong attached to the rider, configured to be driven along the cylindrical body towards the proximal end by pushing on the push button moving the first ratchet rack towards the proximal end, but to disengage the ratchet rack when the push button is retracted by the spring.

The spring may be a helical spring positioned around the neck, between the distal cap and the push button and configured to urge the push button away from the distal cap.

In some embodiments, the toothed prong comprises at least one tooth for engaging at least one serration in the first ratchet rack.

In one embodiment, the toothed prong comprises two teeth for engaging two serrations in the first ratchet rack.

In one embodiment, the first ratchet rack has serrations at a separation for releasing fixed dosages in the range of from about 0.02 ml to about 0.1 ml.

Typically, the stopping mechanism comprises a second ratchet rack fixed to the syringe cylindrical body and configured to engage a second toothed prong fixed to the rider to prevent the rider moving distally along the cylindrical body.

Optionally the syringed body is configured to allow the second toothed prong to slide along the second ratchet rack in a proximal direction.

Typically, the second toothed prong comprises at least one tooth for engaging at least one serration of the second ratchet rack.

In one embodiment, the second toothed prong comprises two teeth for engaging two of serrations of the second ratchet rack.

Preferably, the syringe cradle comprises finger knobs on the outside of the cylindrical body.

Optionally, the finger knobs may be positioned at a plurality of positions along the cylindrical body.

In some embodiments, the syringe cradle comprises an opening such as a slot or a slit along one side of the cylindrical body to allow an operator to view a syringe therein.

In one embodiment, the syringe cradle is configured for engaging a 0.1 ml micro-syringe and for releasing fixed dosages in the range of from about 0.02 ml to about 0.1 ml.

A second aspect of the invention is directed to a method of providing a plurality of fixed doses from a syringe comprising the steps of: (a) Providing a syringe cradle for holding a syringe, the syringe cradle comprising a proximal end for engaging a barrel of a syringe and a rider for pressing on a plunger of the syringe, a cylindrical body for surrounding the syringe, a distal cap for closing a distal end of the cylindrical body, a stepwise advancing mechanism for advancing the rider along the cylindrical body towards the proximal end, and a stopping mechanism to prevent the rider from moving backwards towards the distal end of the cylindrical body; (b) Inserting a syringe of a fluid having a hollow needle attached into the syringe cradle; (c) Inserting a tip of the hollow needle into a patient; (d) Depressing the push button to inject a dose into the patient; (e) Releasing the push button; (f) Removing the tip of the hollow needle from the patient, and (g) Repeating steps (c) to (f).

BRIEF DESCRIPTION OF FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawings making apparent to those skilled in the art how the several forms of the invention may be embodied in practice.

In the accompanying drawings.

DESCRIPTION OF EMBODIMENTS

Figure 1:
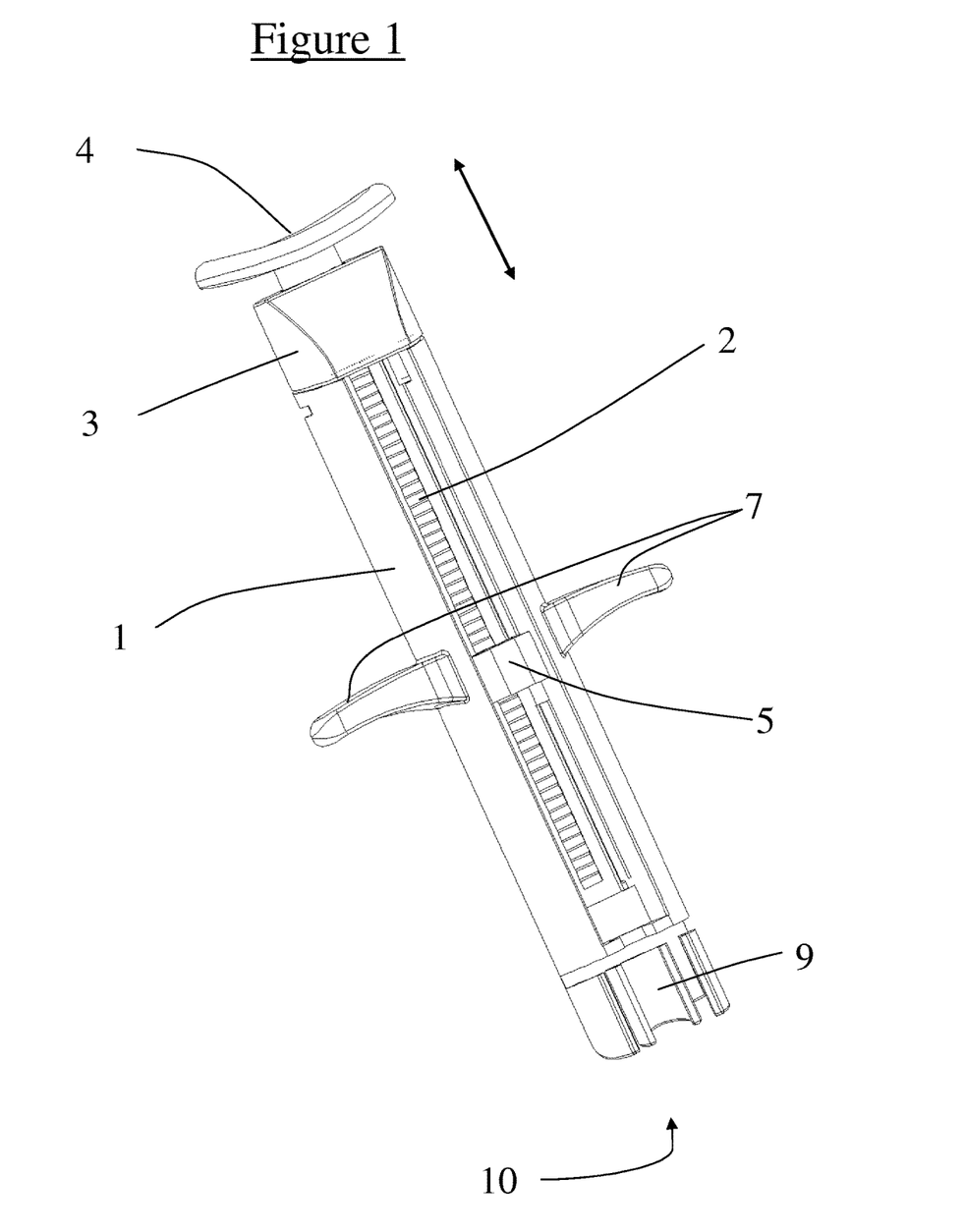
FIG. 1 is an isometric view of a syringe cradle in accordance with one embodiment of the invention.
Figure 2:
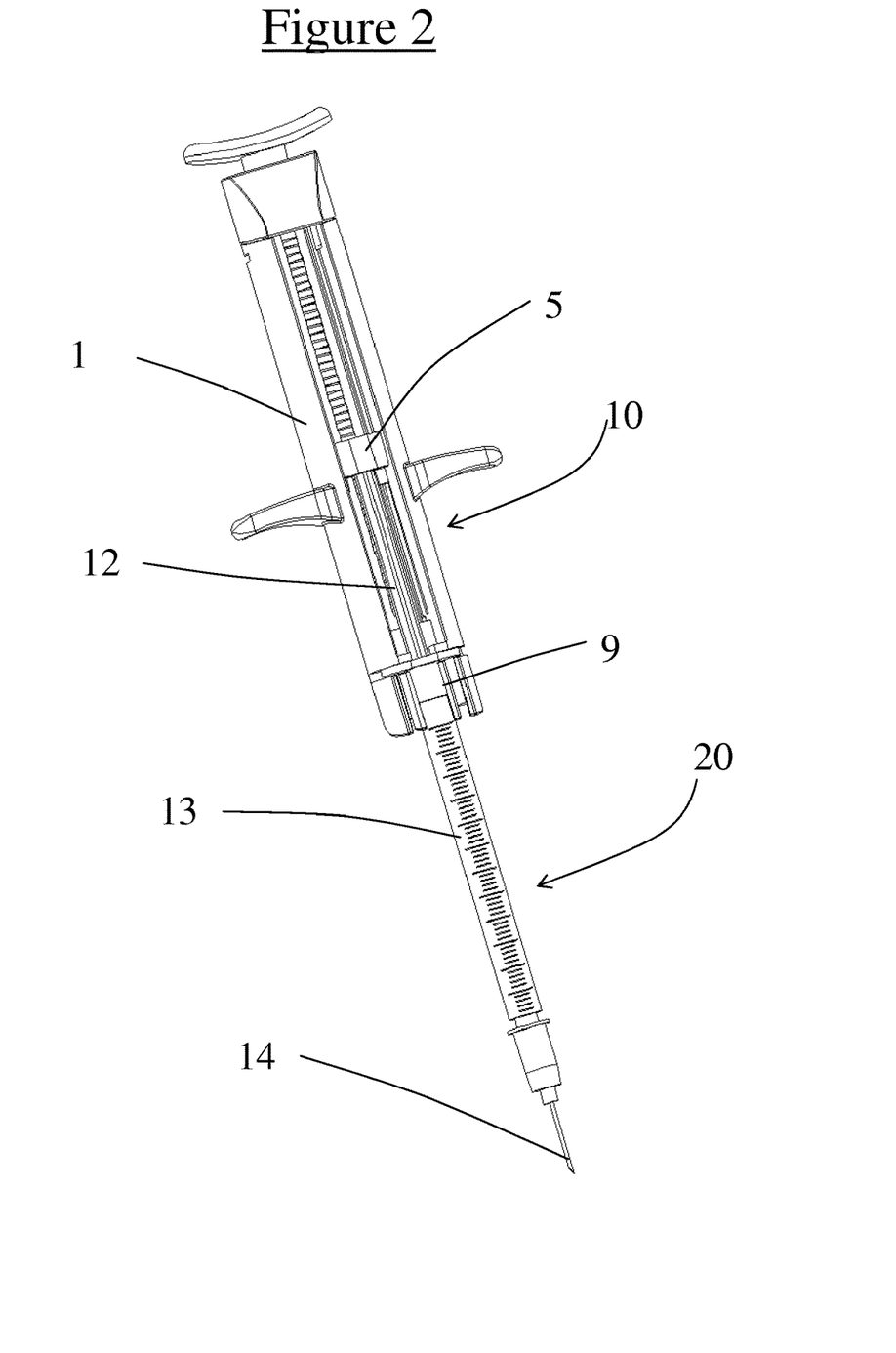
FIG. 2 shows the syringe cradle of FIG. 1 with a syringe attached thereto.

With reference to the Figures, and in particular to FIGS. 1 and 2, a syringe cradle 10 for holding a syringe is shown. FIG. 1 is an isometric view of a syringe cradle in accordance with one embodiment of the invention, and FIG. 2 shows the syringe cradle of FIG. 1 with a syringe attached thereto.

The syringe cradle 10 comprising a syringe holder 9 at a proximal end for engaging the flange 15 around the end of the barrel 13 of a syringe 20 and a rider 5 for pressing on a plunger 12 of the syringe, a cylindrical body 1 for surrounding the syringe, a distal cap 3 for closing a distal end of the cylindrical body, a stepwise advancing mechanism 35 for advancing the rider 5 (FIG. 3) along the cylindrical body 1 of the syringe cradle 10 towards the proximal end thereof, and a stopping mechanism 45 to prevent the rider 5 from moving backwards towards the distal end of the cylindrical body 1.

Also shown in FIG. 1 is a push button 4 and finger knobs 7 on the syringe cradle 10, and in FIG. 2, a hollow needle 14 attached to the barrel 13 of the syringe.

Figure 3:
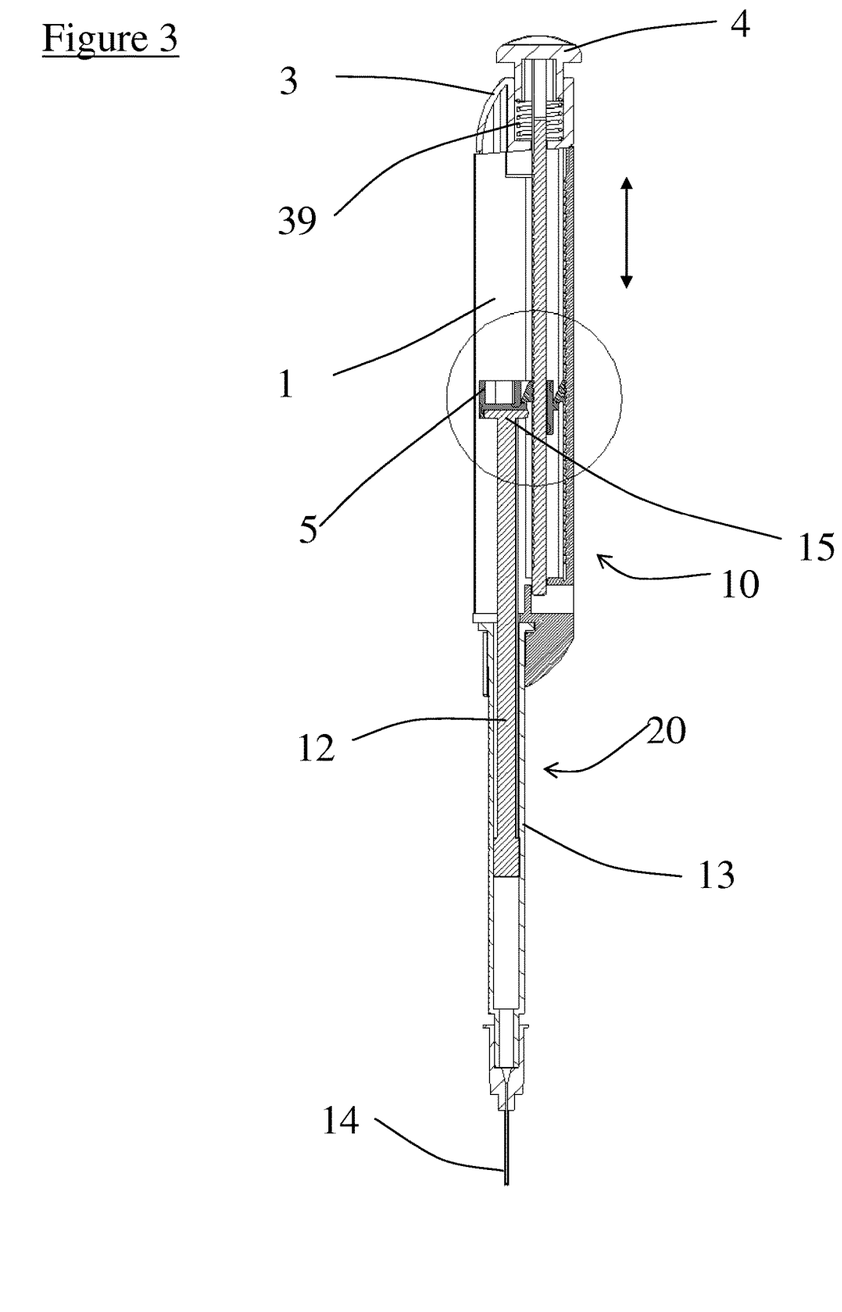
FIG. 3 is a cross-section through the syringe holder and syringe of FIG. 2.

FIG. 3 is a cross-section through the syringe cradle 10 and syringe 20 of FIG. 2.

Figure 4A:
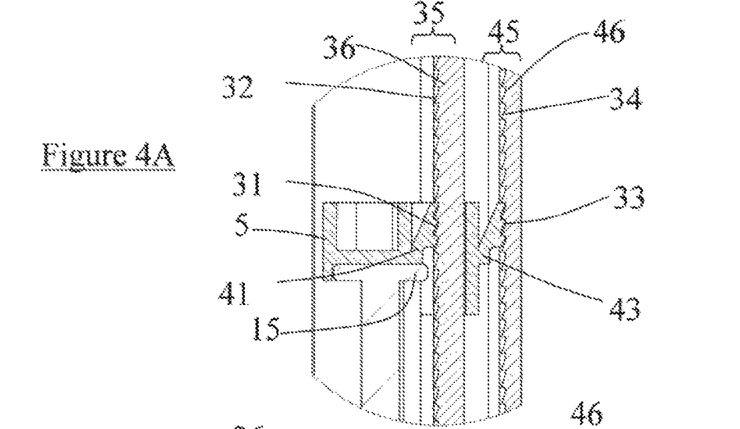
FIG. 4A is an enlargement of the rider 15 of FIG. 3, showing first and second ratchet racks, and teeth of the first and second toothed prongs engaging the serrations of the first and second ratchet racks.
Figure 4B:
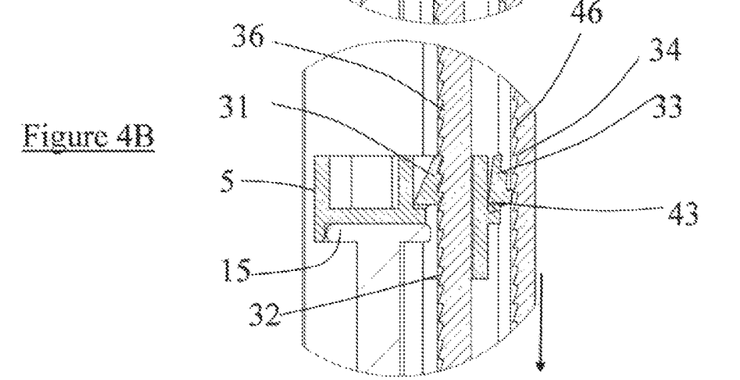
FIG. 4B is an enlargement of the rider 15 showing teeth 31 of the first toothed prong 41 engaging the serrations of the first ratchet rack 36 and the teeth 33 of the second toothed prong 43 tilted about its seating to not engage but to slip past a second ratchet rack 46 that is fixed to the cradle cylinder 1.
Figure 4C:
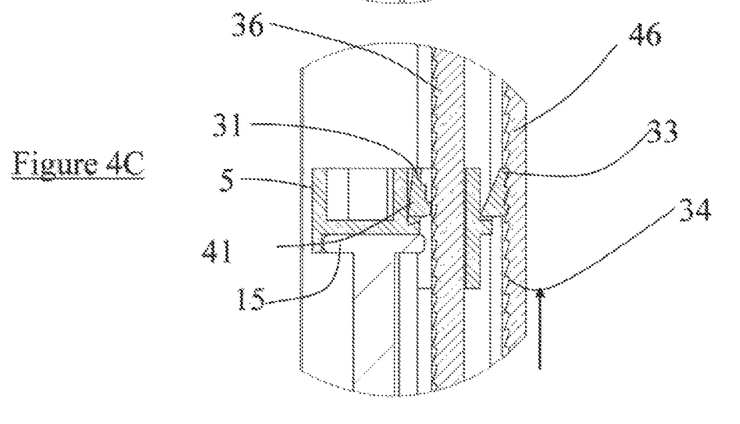
FIG. 4C is an enlargement of the rider 15 showing teeth 31 of the first toothed prong 41 tilted about its seating to not engage but to slip past the serrations 32 of the first ratchet rack 36 and the teeth 33 of the second toothed prong 43 resting on its seating to engage the serrations 34 of the second ratchet rack 45 that is fixed to the cradle cylinder 1.

FIG. 4A is an enlargement of the rider 5 of FIG. 3, according to one embodiment showing first and second ratchet racks 36, 46 and first and second toothed prongs 41, 43 whose teeth 31, 33 engage the serrations 32, 34 of the first and second ratchet racks 36, 46. FIG. 4B is an enlargement of the rider 5 showing teeth 31 of the first toothed prong 41 engaging the serrations 32 of the first ratchet rack 36, and the teeth 33 of the second toothed prong 43 tilted about its seating to not engage but to slip past the teeth 34 of a second ratchet rack 46 that is fixed to the cradle cylinder 1. FIG. 4C is an enlargement of the rider 5 showing teeth 31 of the first toothed prong 41 tilted about its seating to not engage but to slip past the serrations 32 of the first ratchet rack 36 and the teeth 33 of the second toothed prong 43 resting on its seating to engage the serrations 34 of the second ratchet rack 46 that is fixed to the cylinder 1 of the syringe cradle 10.

With reference to FIG. 3 and FIGS. 4A-4C, in one embodiment, the stepwise advancing mechanism comprises a push button 4 coupled to a first ratchet rack 36 by a neck 6 passing through an aperture in the distal cap 3 and a spring 39 (FIG. 3) configured to urge the push button 4 away from the distal cap 3, and a first toothed prong 41 attached to the rider 5, configured to be driven along the cylindrical body 1 towards the proximal end in the direction of the syringe holder 9 and needle 14 by pushing on the push button 4, moving the first ratchet rack 36 towards the proximal end, but to disengage the first ratchet rack 36 when the push button 4 is retracted by the spring 39.

The spring 39 may be a helical spring positioned around the neck 6, between the distal cap 3 and the push button 4 and configured to urge the push button 4 away from the distal cap 3.

In some embodiments, the toothed prong 41 comprises at least one tooth 31 for engaging at least one serration 32 in the first ratchet rack 36.

In one embodiment, the toothed prong 41 comprises two teeth 31 for engaging two serrations 32 in the first ratchet rack 36. Using two teeth 31 to engage two serrations 32 adds an additional safety factor.

In one embodiment, the first ratchet rack 36 has serrations 32 at a separation for releasing fixed dosages in the range of from about 0.02 ml to about 0.1 ml.

Figure 5A:
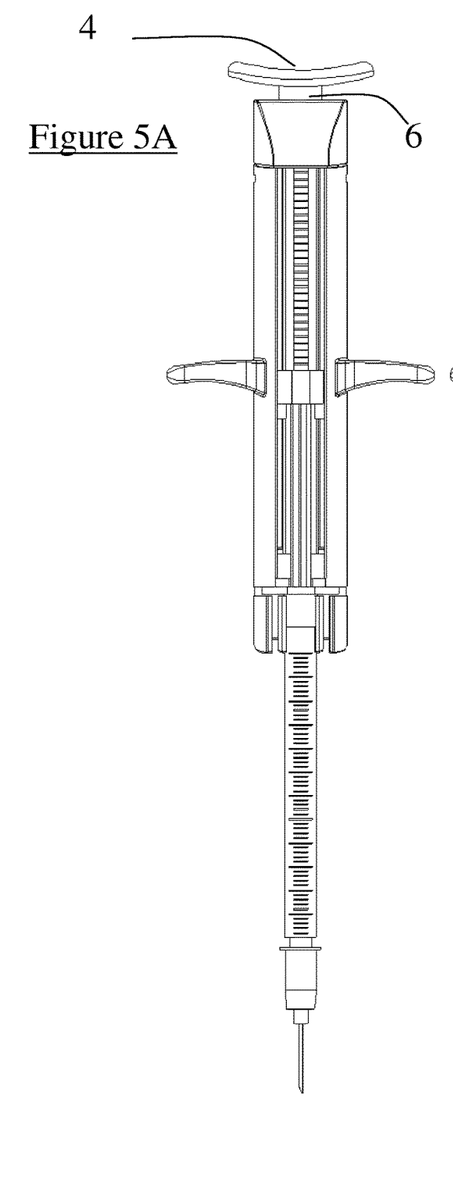
FIG. 5A shows the push button 4 in its released configuration, urged away from the cap 3 by the spring 39 (not shown) showing the neck 6 thereunder.
Figure 5B:
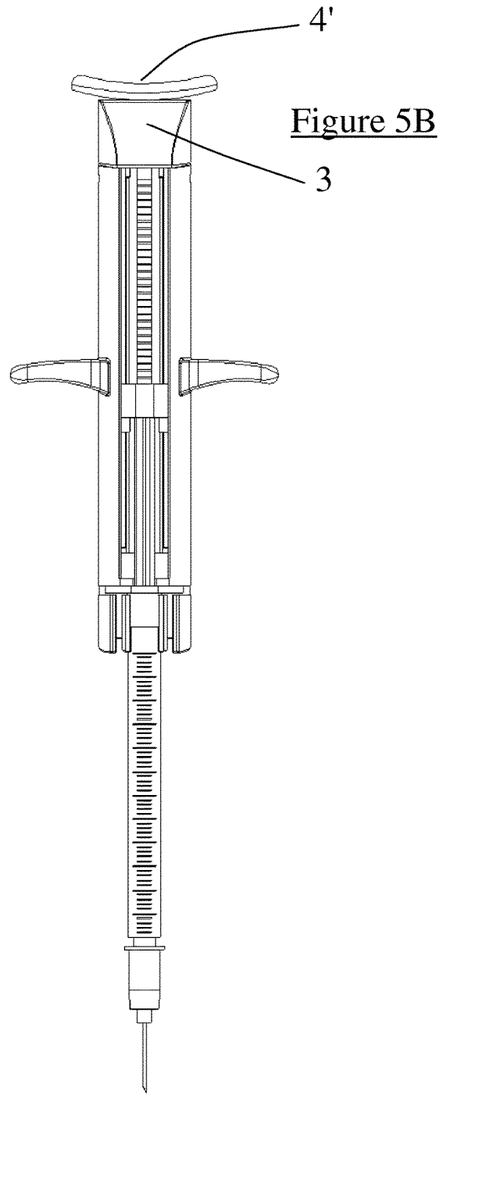
FIG. 5B shows the push button 4 in its depressed configuration, pushed against the cap 3.

With particular reference to FIGS. 4A and 5B, on depressing the push button 4, the first ratchet rack 36 transmits a downwards force on the teeth 31 of a first toothed prong 41 that pushes on rider 5 and thereby exerts a force on the end 15 of the plunger 12.

When pressure is released on the push-button 4 (FIG. 5A), it is returned to its extended position by the spring 39 (FIG. 3), retracting the first ratchet rack 36. The toothed prong 41 can rock about seating with respect to the rider 5 so that the teeth 31 thereof disengage the serrations 32 of the first ratchet rack 36 to assume the configuration 31 shown in FIG. 4C.

In one embodiment, first toothed prong 41 may be fixed to rider 5 by its seating. In another embodiment, the prong 31 may be a separate component that simply sits on the rider 5.

Typically, the stopping mechanism comprises a second ratchet rack 46 fixed to the syringe cylindrical body 1 and configured to engage a second toothed prong 43 fixed to the rider 5 to prevent the rider 5 moving distally along the cylindrical body 1.

As shown in FIG. 4B, the syringe cradle 10 may be configured to allow the second toothed prong 43 to tilt with respect to its seating to slide along the second ratchet rack 46 in a proximal direction such that the teeth 33 of the second toothed prong 43 do not engage serrations 34 of the second rack 46.

Typically, the second toothed prong 43 comprises at least one tooth 33 for engaging at least one serration 34 of the second ratchet rack 46. The second toothed prong 43 may be fixed to its seating and may be integral to rider 5, or may be a separate component that simply sits on the rider 5 (as shown in FIGS. 4B and 4C).

As shown in FIGS. 4A-4C, the second toothed prong 43 may comprise two teeth 33 for engaging two of serrations 34 of the second ratchet rack 46, providing an additional degree of safety.

Referring back to FIG. 1, preferably, the syringe cradle 1 comprises finger knobs 7 on the outside of the cylindrical body 1 to facilitate gripping. In use, the operator will generally press on the push button 4 with a thumb or with the palm of the hand at the base of the thumb, and engage the finger knobs with the index and middle fingers.

Figure 6A:
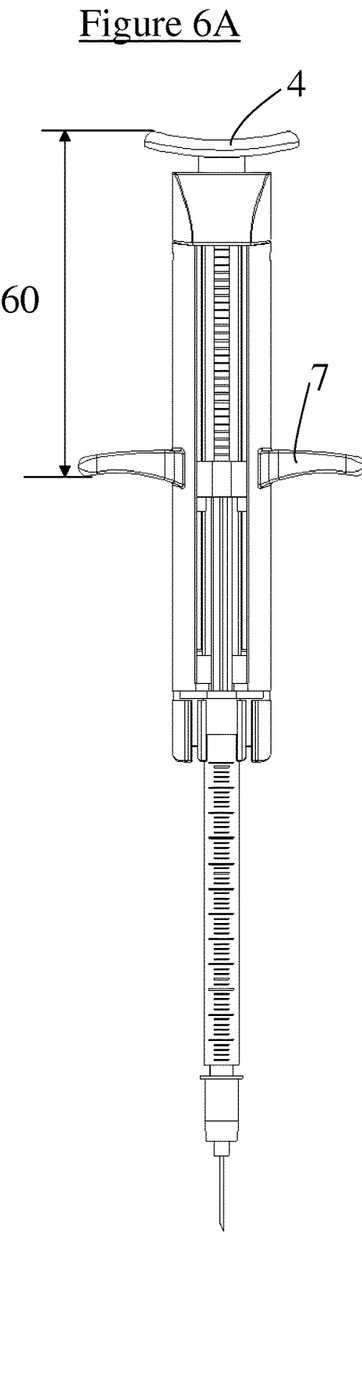
FIG. 6A shows the finger knobs set at a short distance 60 from the released push button.
Figure 6B:
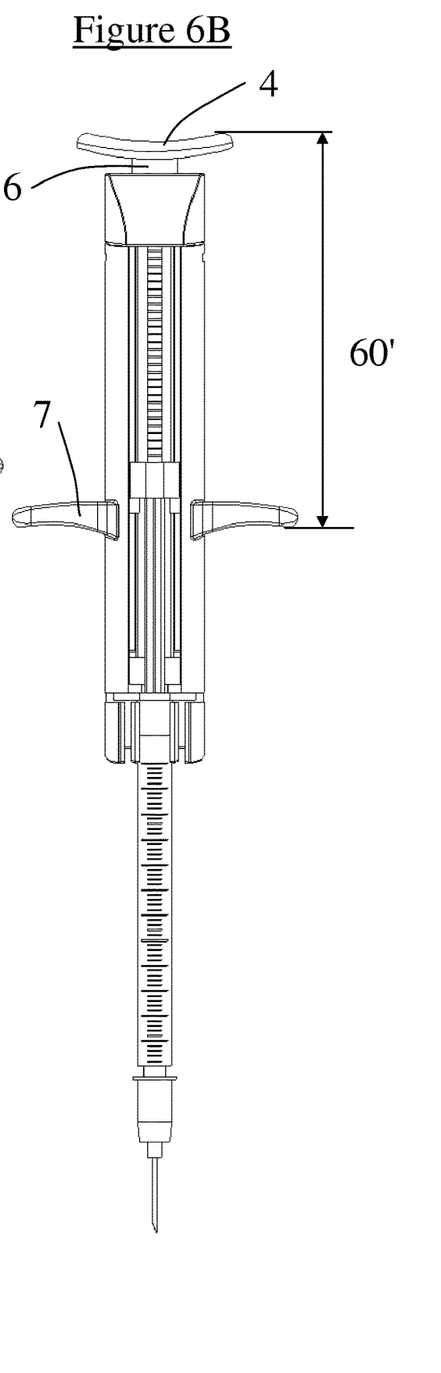
FIG. 6B shows the finger knobs set at a longer distance 60' from the released push button.

With reference to FIGS. 6A and 6B, in some embodiments, the position of the finger knobs 7 may be varied over a plurality of positions along the cylindrical body 1. For example, the finger knobs 7 may be provided on a separate ring clip that fits onto the cylindrical body 1, perhaps having protrusions that engage corresponding dimples on the cylindrical body so that the distance from the push button 4 to the finger clips 7 may vary over a range 60, 60'.

In some embodiments, the syringe cradle 10 comprises an opening such as a slot or a slit along one side of the cylindrical body 1 to allow an operator to view the rider 5 and plunger 12 of a syringe therein.

In one embodiment, the syringe cradle 10 is configured for engaging a 0.1 ml micro-syringe and for releasing fixed dosages in the range of from about 0.02 ml to about 0.1 ml.

Figure 7:
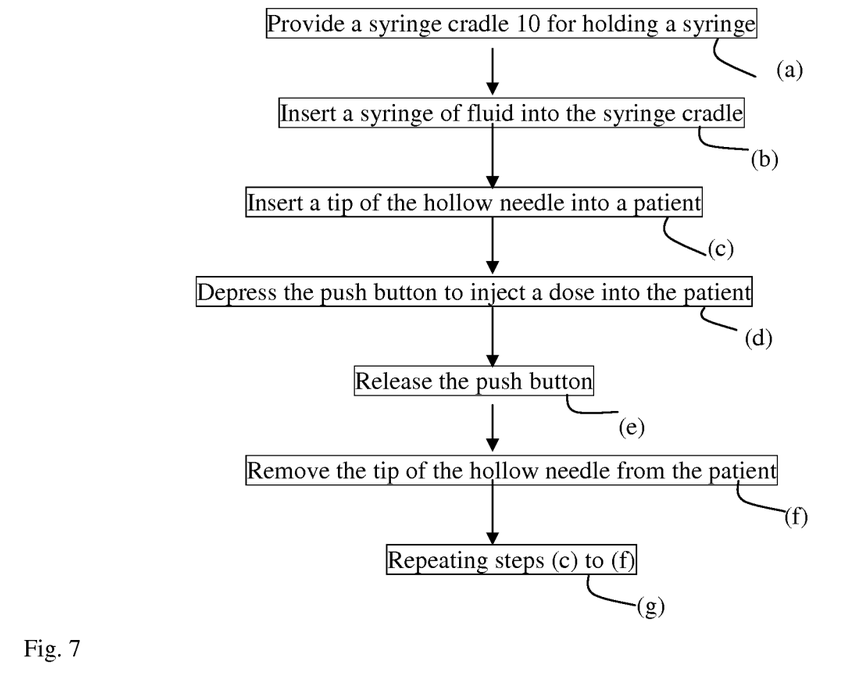
FIG. 7 is a flowchart illustrating use of the syringe cradle.

With reference to FIG. 7, a second aspect of the invention is directed to a method of providing a plurality of fixed doses from a syringe comprising the steps of: (a) Providing a syringe cradle 10 for holding a syringe, the syringe cradle 10 comprising a proximal end with a syringe holder 9 for engaging a barrel 13 of a syringe and a rider 5 for pressing the end of 35 of a plunger 12 of the syringe, a cylindrical body 1 for surrounding the syringe, a distal cap 3 for closing a distal end of the cylindrical body 1, a stepwise advancing mechanism for advancing the rider 15 along the cylindrical body 1 towards the proximal end, and a stopping mechanism to prevent the rider from moving backwards towards the distal end of the cylindrical body 1; (b) Inserting a syringe of a fluid having a hollow needle 14 attached into the syringe cradle 10; (c) Inserting a tip of the hollow needle into a patient; (d) Depressing the push button 4 to inject a dose into the patient; (e) Releasing the push button 4; (f) Removing the tip of the hollow needle 14 from the patient, and (g) Repeating steps (c) to (f).

Although described above as a convenient syringe cradle for holding a botox micro-syringe, it will be appreciated that the present invention may be useful for other applications where a series of controlled micro-dosages are injected, such as for injecting tattoo inks, for example.

Thus the scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A syringe cradle for holding a syringe, the syringe cradle comprising
 a syringe holder at a proximal end for engaging a barrel of a syringe and a rider for pressing on a plunger of the syringe,
 a cylindrical body for surrounding the syringe,
 a distal cap for closing a distal end of the cylindrical body,
 a stepwise advancing mechanism for advancing the rider along the cylindrical body towards the proximal end, and a stopping mechanism to prevent the rider from moving backwards towards the distal end of the cylindrical body, wherein the stepwise advancing mechanism comprises a push button coupled to a first ratchet rack on a side of the rider by a neck passing through an aperture in the distal cap and a spring configured to urge the push button away from the distal cap, and a first toothed prong attached to the rider, configured to be driven along the cylindrical body towards the proximal end by pushing on the push button moving the first ratchet rack towards the proximal end, but to disengage the ratchet rack when the push button is retracted by the spring, and where the stopping mechanism comprises a second ratchet rack fixed directly to the syringe cylindrical body and configured to engage a second toothed prong fixed directly to the rider to prevent the rider moving distally along the cylindrical body.

2. The syringe cradle of claim 1 wherein the spring is a helical spring positioned around the neck, between the distal cap and the push button and configured to urge the push button away from the distal cap.

3. The syringe cradle of claim 1, wherein the stopping mechanism is configured to allow the second toothed prong to slide along the second ratchet rack in a proximal direction.

4. The syringe cradle of claim 1, wherein the second toothed prong comprises a plurality of teeth for engaging a plurality of serrations of the second ratchet rack.

5. The syringe cradle of claim 1, wherein the second toothed prong comprises two teeth for engaging two serrations of the second ratchet rack.

6. The syringe cradle of claim 1, configured for engaging a 0.1 ml micro-syringe and for releasing fixed dosages in the range of from about 0.02 ml to about 0.1 ml.

7. The syringe cradle of claim 1, wherein the first ratchet rack has serrations at a separation for releasing fixed dosages in the range of from about 0.02 ml to about 0.1 ml.

8. The syringe cradle of claim 1 wherein the first toothed prong comprises a plurality of teeth for engaging a plurality of serrations in the first ratchet rack.

9. The syringe cradle of claim 8, wherein the plurality of teeth of the first toothed prong comprises two teeth for engaging two serrations in the first ratchet rack.

10. The syringe cradle of claim 1, further comprising finger knobs on the outside of the cylindrical body.

11. The syringe cradle of claim 10 wherein the finger knobs are positionable at a plurality of positions along the cylindrical body.

12. The syringe cradle of claim 1, comprising an opening along one side of the cylindrical body to allow an operator to view a syringe therein.

13. The syringe cradle of claim 12 wherein the opening is selected from the group comprising of a slot and a slit.

14. A method of providing a plurality of fixed doses from a syringe comprising the steps of:
 (a) providing a syringe cradle of claim 1;
 (b) inserting a syringe of a fluid having a hollow needle attached into the syringe cradle;
 (c) inserting a tip of the hollow needle into a patient;
 (d) depressing the push button to inject a dose into the patient;
 (e) releasing the push button;
 (f) removing the tip of the hollow needle from the patient, and repeating steps (c) to (f).

* * * * *